United States Patent [19]
Doerig

[11] 3,935,065
[45] Jan. 27, 1976

[54] PROCEDURE FOR CONSERVATION OF LIVING ORGANS AND APPARATUS FOR THE EXECUTION OF THIS PROCEDURE

[76] Inventor: Roland Karl Doerig, Nordstrasse 350, CH-8037, Zurich, Switzerland

[22] Filed: Aug. 29, 1973

[21] Appl. No.: 392,441

Related U.S. Application Data

[62] Division of Ser. No. 285,739, Sept. 1, 1972.

[30] Foreign Application Priority Data

Sept. 2, 1971 Switzerland.................. 13000/71
Mar. 24, 1972 Switzerland.................. 4479/72

[52] U.S. Cl. ................................................ 195/1.7
[51] Int. Cl.² ........................ C12B 3/00; C12B 9/00
[58] Field of Search .................................... 195/1.7

[56] References Cited
UNITED STATES PATENTS

| 3,632,473 | 1/1972 | Belzer | 195/1.7 |
| 3,738,914 | 6/1973 | Thorne et al. | 195/1.7 |
| 3,772,153 | 11/1973 | Roissart | 195/1.7 |
| 3,777,507 | 12/1973 | Burton et al. | 195/1.7 |

OTHER PUBLICATIONS

Eiseman et al., Surgery, Vol. 60 (Dec. 1966) pp. 1183–1186.

*Primary Examiner*—Norman A. Drezin
*Attorney, Agent, or Firm*—McGlew and Tuttle

[57] ABSTRACT

Apparatus and process are provided for the conservation of living organs by using a cooled perfusing means enriched with a respiratory gas in a thermally insulated receptacle with a pumping device driven by a gas and which regulates the perfusing medium according the flow-resistance in the organ.

2 Claims, 4 Drawing Figures

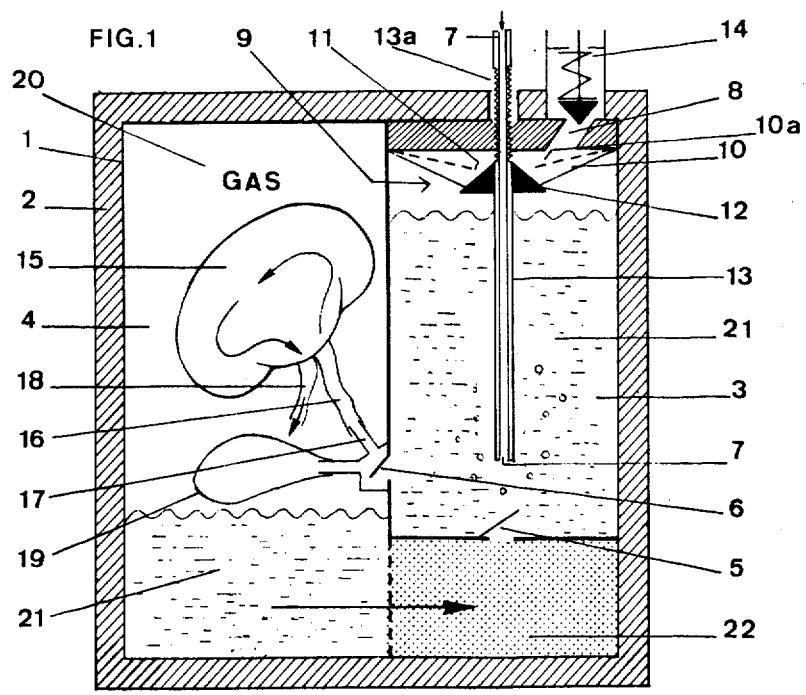
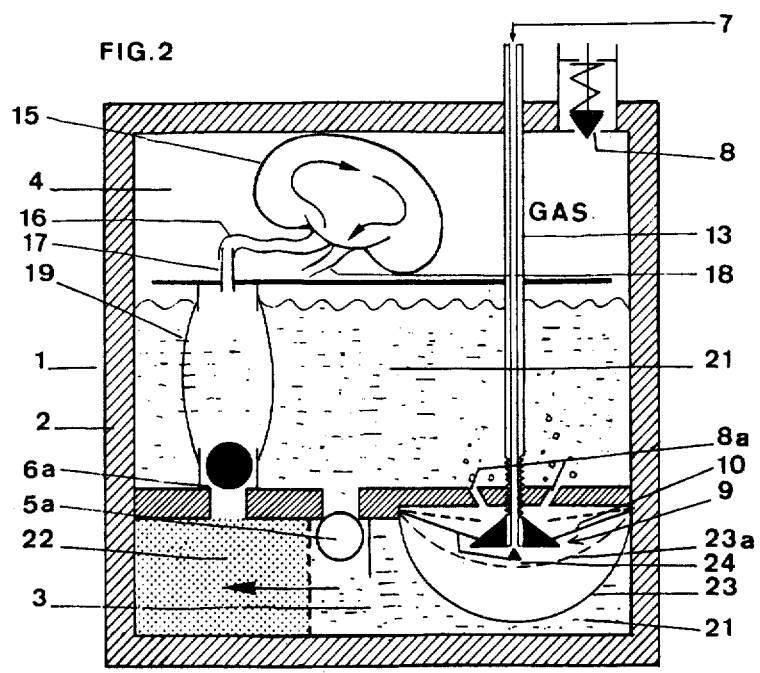

PROCEDURE FOR CONSERVATION OF LIVING ORGANS AND APPARATUS FOR THE EXECUTION OF THIS PROCEDURE

This is a division of application Ser. No. 285,739 filed Sept. 1, 1972.

The invention concerns a procedure for preservation of living organs by using a cooled perfusion enriched with a respiratory gas as well as an apparatus for the execution of this procedure.

The existing apparatus for perfusion and for the conservation of organs are mainly used for stationary operating due to their size and large weight and because electric energy is needed for running them. Another disadvantage is the fact that the rate of flow of the perfusion pump is manual and fixed by the circumstance that the living organ is endangered, if the pressure of solution in the vessel rises.

The main problem is that the organs have to be transported, because the donor and the receptor of a living organ, e.g., a human kidney, are usually in different places. Therefore it is often not possible to use the offered organ because without preservation an organ remains vital only for a very short time and transport in the existing devices is not possible due to the aforementioned reasons.

The present invention solves the problem and removes this disadvantage of the existing devices. The invention makes it possible to produce a portable, apparatus for perfusion, independent from electricity and with pumping characteristics that save the organ, with all the necessary provisions for regulation.

This invention is characterisized by automatic regulation of the perfusion which is adapted to the flow resistance in the organ, using a perfusing pump, which is driven by a gas, e.g. by a respiratory gas.

The operation of the perfusion pump and the cooling of the perfusate are achieved by $CO_2$-gas resulting from dry ice. The dry ice can even be used to run a pumping device to oxygenate the perfusate. The cooling temperature of the perfusate is kept constant by changing the position or the insulation of the dry ice compartment in relation to the organ and pump compartment.

The operation of the perfusion pump may be changed from the $CO_2$-gas to a respiratory gas. In this case, the respiratory gas after passing the pump is used to oxygenate the perfusuate. The apparatus for the execution of this procedure is characterised by a thermally insulated receptacle which contains one compartment for the pump, one for the organ and, if necessary, one for the dry ice. The pump compartment is provided with an inflow and an outflow valve for the perfusate; the gas enters through a gas inlet and is vented through a pressure or volume monitored outlet valve.

Further the device is provided with regulators for monitoring the physiologic pulse form, the pulse frequency, the rate of flow and the maximal pressure of perfusion for a pulsating or non pulsating organ perfusion, as well as for operating under hyperbaric conditions in the organ compartment.

In the drawings examples for the execution of the invention are illustrated.

FIG. 1 shows a section through a perfusion apparatus with a pressure monitored outlet valve for the gas.

FIG. 2 shows a variation of the perfusion apparatus in FIG. 1.

Figure 3:
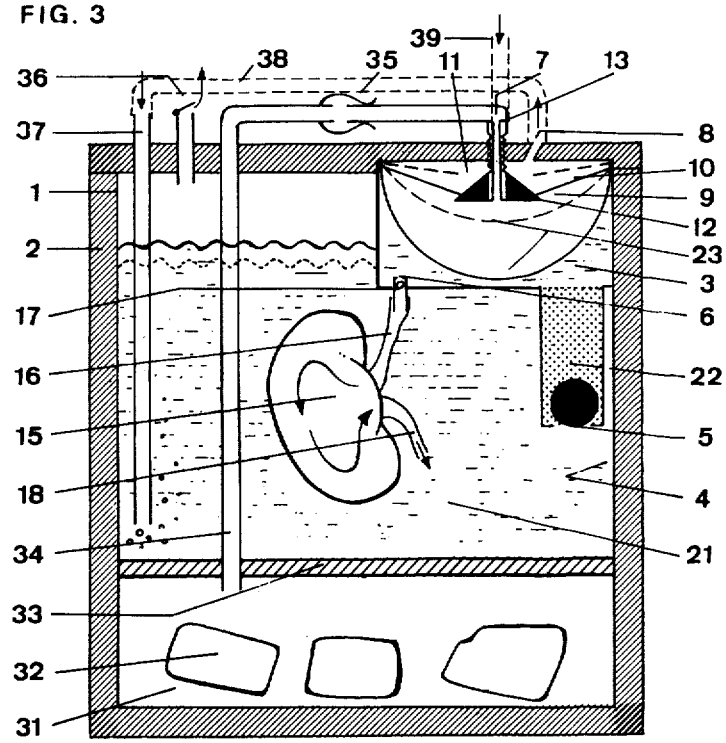
FIG. 3 shows a perfusion apparatus driven by dry ice.

The apparatus for perfusion shown in FIG. 1 consists of a receptacle with thermoinsulation 2. It is divided into a pumping compartment 3 and an organ compartment 4. In the pump compartment 3 there are the passive inflow valve 5 and the passive outflow valve 6 for the perfusate 21, the gas inlet 7 and the gas outlet 8 as well as the pressure monitored outlet valve 9 for the gas. The latter is composed of a mobile part in the form of a prestressed monostabile membrane 10 with an opening 11 for the gas and a fixed part 12, the valve fitting. A monostabile membrane is a membrane, which after deflecting to one side returns automatically into the original position.

The gas inlet 7 is directed through a tube 13 which carries the fixed part 12 of the outlet valve 9 for the gas. This tube 13 is inserted with an outer thread 13a into an inner thread on the receptacle 1. By turning the tube 13 the position of the part 12 and at the same time the stressing of the membrane 10 can be changed. Above the gas outlet 8 a surplus-pressure valve 14 is mounted.

The organ compartment 4 includes the organ 15, which is to be conserved. This organ is connected with its artery 16 to a linking tube 17 for the perfusate. The vein 18 is open to the organ compartment 4. A section of the linking tube 17 is elastically widened (19). The organ 15 enclosed in the organ compartment 4 is subjected to the pressure of an air cushion 20. The liquid for perfusion, shortened to "the perfusate" 21, has a different level in the pumping compartment 3 to that in the organ compartment 4. A filter 22 is installed in the perfusion circuit.

The apparatus for perfusion functions in the following way: From a pressure flask, not shown in the drawings, a respiratory gas enters the tube 13 through the gas inlet 7 and continues from there to the pump compartment 3, where it bubbles through the perfusate 21, which is thereby enriched with the gas. The gas is collected above the perfusate and, if the outlet valve 9 for the gas is closed, builds up a pressure in the pump compartment 3. This pressure pumps the perfusate through the passive outflow valve 6 via the linking tube 17 into the artery 16 of the organ 15. The organ is perfused in direction of the arrows. The perfusate flows out of the vein 18 into the organ compartment 4, where it collects at the bottom. By increasing the volume of the perfusate in the organ compartment the overlying air cushion 20 becomes compressed. By achieving the desired pressure in the organ compartment 3 the prestressed membrane 10 is suddenly lifted from the fixed part 12 of the outlet valve 9 and takes position 10a. The gas is vented through the opening 11 and the gas outlet 8. The pressure in the pump compartment 3 decreases. The previously compressed air cushion 20 in the organ compartment 4 pushes the perfusate through the inflow valve 5 back into the pump compartment 3. By running through the filter 22 the perfusate is cleaned. As soon as the pressure in the organ compartment 4 and in the pump compartment 3 falls to the original level, the membrane 10 returns to the starting position 10 and closes the outlet valve 9 for the gas. The gas is still running through the gas inlet 7 and a new pumping rate starts. By turning the tube 13 the stressing of the membrane 10 can be changed. If the fixed part 12 on the outlet valve 9 is lifted, the valve 9 already opens at a lower pressure. By this means the maximal pulse pressure can be lowered, the rate of flow reduced and the pulse frequency raised. The pulse form and the volume of perfusion per time unit are monitored according to these conditions. They can also be altered in a similar manner by regulating the gas inflow. If the flow resistance in the organ 15 rises, then, at a constant gas inflow, the desired pressure in the pump compartment 3 is reached sooner and after a smaller rate of flow per pumping stroke. By means of the pressure monitored membrane 10 the pump regulates automatically, like a heart, the pulse frequency and the rate of flow adapted to the flow resistance in the organ 15. The maximal pulse pressure per pumping stroke is unchanged. This safely avoids the dangerous destruction of the organ 15 caused by over pressure during perfusion. As a further advantage the best corresponding volume of flow in relation to the organ resistance is maintained. The elastic sections 19 in the wall of the linking tube 17 for the perfusate, mounted after the outflow valve 6, absorb the pulse strokes and, if the elasticity is very high, a pulseless, continous perfusion of the organ can be achieved, despite the pulsations from the pump.

A surplus-pressure valve 14 is provided at the gas outlet 8 to obtain a hyperbaric perfusion.

In contrast to FIG. 1 referring now to the perfusion apparatus shown in FIG. 2, the gas, after entering through the tube 13, is separated from the perfusate 21 by an elastic membrane 23. The gas collects between membrane 10 and the elastic membrane 23 until the pressure opens the gas-outlet valve 9. The gas is vented through the gas outlet 8a and bubbles through the perfusate into the organ compartment 4. The counterpressure is effected by the contracting elastic membrane 23. The gas pressure pushes the perfusate from the pump compartment 3 through the filter 22, via outflow-valve 6a and the elastic enlargement 19 of the linking tube 17 into the artery 16 of the Organ 15. After perfusing the Organ in direction of the arrows the perfusate flows out of the vein 18 into the organ compartment 4 and from there via inflow-valve 5a in the pump compartment 3.

At the membrane 10 an additional inlet-valve 24 for the gas is mounted, which at the end of a pumping stroke is lifted together with the opening membrane 10 and closes the gas inlet on the tube 13. By this means the gas-supply is interrupted until the next pumping stroke and the driving gas can be economized.

The perfusion-apparatus shown in FIG. 3, contrary to the other two models can be driven with $CO_2$-gas resulting from dry ice 32 or with a respiratory gas from a pressure flask. Besides the pump compartment 3 and the organ compartment 4 there is an additional pressure compartment 31 for the dry ice 32. This dry-ice-compartment 31 is thermally insulated against the organ compartment 4 by the insulation 33. A tube 34 is joined to the compartment 31 by the connection 13 on the gas inlet 7. The gas entering through the tube 13 is separated from the perfusate 21 by an elastic membrane 23 as in FIG. 2. For the oxygenation of the perfusate with air an air-outlet valve 36 and an air-inlet-tube 37 are provided. They open the organ compartment 4 to the open air outside. For operation with respiratory gas from a pressure flask, e.g. if they lack dry ice in a hospital, the connections illustrated by dashed lines are necessary: A linking tube 38 between air-inlet-tube 37 and gas-outlet 8 as well as a connection 39 to a pressure flask not shown in the drawings. A surplus-pressure valve 35 in the linking tube 34 may be mounted for safety.

The apparatus for perfusion in FIG. 3 functions in the following way: The $CO_2$-gas resulting from the dry ice 32 in compartment 31 by warming up, runs through the linking tube 34 into the gas inlet 7 of the perfusion pump and causes a pressure on the elastic membrane 23, if the gas-inlet valve 9 is closed. The perfusate 21 is thereby transported from the pump compartment 3 through the outflow-valve 6 into the artery 16 of the organ 15. The perfusate flowing out of the vein 18 raises the level of the perfusate in the organ compartment 4 and presses the air in the upper part of the compartment 4 out through the air-outlet valve 36. The prestressed membrane 10 is suddenly lifted from the valve fitting 12, if the desired pressure is achieved in the pump compartment 3. The $CO_2$-gas is vented through the opening 11 and the gas-outlet 8. The elastic membrane 23, liberated from the gas pressure, contracts and the perfusate 21 flows from the organ compartment 1, via inflow-valve 5 and filter 22 in the pump compartment 3. The level of the perfusate in the organ compartment 4 falls back to the position illustrated by dashed lines. A low pressure is built up in the upper part of the organ compartment 4 if the air-outlet valve 36 is closed. The air from outside is sucked in through the air-inlet-tube 37, bubbles through the perfusate 21 and oxygenates it. If the pressure in the pump compartment 3 is lowered to the original value, the membrane 10 returns to the starting position and closes the gas-outlet valve 9. The driving gas continues to run through the gas inlet 7 and a new pumping rate starts. In this way the perfusion apparatus works completely automatically as long as there remains any dry ice in compartment 31.

If necessary the perfusion apparatus may be run with a respiratory gas from a pressure flask. In this case the linking tube 34 is moved from the connection 13 and replaced by the connecting-tube 39, which leads to the flask containing the respiratory gas. The gas-outlet 8 on the pump compartment 3 is joined to the air-inlet-tube 37 via connecting-tube 38, which conducts the vented respiratory gas into the organ-compartment 4, where it bubbles through the perfusate 21 and oxygenates it. The air is vented through the air-outlet valve 36. The necessary cooling in this arrangement is effected with normal ice in compartment 31, i.e. if using a respiratory gas for operation. The perfusing pump works in just the same way as when operating with dry ice. The desired, constant cooling temperature of the perfusate 21 is effected by a corresponding position and insulation of the dry-ice-compartment 31 in relation to the compartment for the organ 4 and the pump 3. The thickness of the insulation 33 is correspondingly selected.

Figure 4:
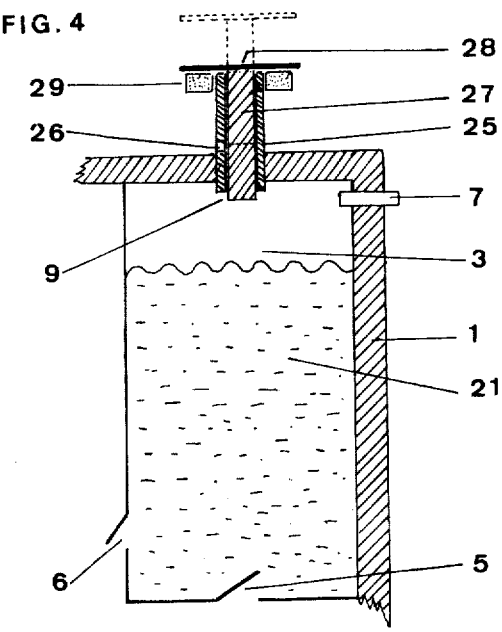
FIG. 4 shows a part of a perfusion apparatus with a magnetic outlet valve.

FIG. 4 shows a variation of the pressure monitored outlet-valve 9 for the gas with a magnetic control. This consists of a fixed cylindrical tube 25 with a lateral gas outlet 26 and of a mobile, inserted bolt 27 on which a holding plate of metal 28 is mounted at the upper end. With help of this plate 28 the bolt 27 is held down by a magnet 29, the magnet being mounted at the upper end of the tube 25 and in this way closing the gas-outlet 26. When the desire pressure in the pump compartment 3 is reached, Then the bolt 27 with holding-plate 28 is suddenly separated from the magnet 29. The bolt 27 is lifted and the gas is vented through the gas-outlet 26. The magnet 29 pulls the bolt 27 downwards and closes the gas-outlet-valve 9 suddenly, if the pressure in the pump-compartment 3 falls to the starting level. The gas supply is achieved through a separated gas-inlet 7. The simple procedure, as well as the low weight and the smal price of the apparatus and the dry-ice, which supplies the energy for cooling, perfusion and oxygenation, the few necessary components for construction together with the completely automatic and safe operating of the apparatus allow a serial-production of a compact, portable safely operating and cheap, disposable perfusion-apparatus in which living human and animal organs can be transported anywhere.

What is claimed is:

1. In a process for the conservation, storage and transport of a living organ using a portable apparatus having an organ compartment, a pump compartment and a cooled liquid perfusion medium enriched with a respiratory gas, wherein said perfusion medium is subjected to automatic regulation of the flow rate of said gas in response to the flow resistance in the organ, the improvement comprising the use of dry ice and the $CO_2$ gas resulting therefrom for the cooling of the perfusate and the operation both of the perfusing pump and of the pumping means for oxygenating the perfusate with air.

2. The process of claim 1, wherein the cooling temperature of the perfusate is kept constant at a desired level by changing either the position of the insulation of a dry ice compartment in relation to the organ compartment and the pump compartment.

* * * * *